US012588855B2

(12) United States Patent
Chen et al.

(10) Patent No.: US 12,588,855 B2
(45) Date of Patent: Mar. 31, 2026

(54) DETERMINATION METHOD AND DETERMINATION APPARATUS FOR BEGINNING OF T-WAVE, STORAGE MEDIUM AND COMPUTER PROGRAM PRODUCT

(71) Applicant: BOE TECHNOLOGY GROUP CO., LTD., Beijing (CN)

(72) Inventors: Xue Chen, Beijing (CN); Jinnv Liu, Beijing (CN); Yude Li, Beijing (CN); Zheng Wu, Beijing (CN); Li Zhou, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 770 days.

(21) Appl. No.: 17/912,643

(22) PCT Filed: Jun. 10, 2021

(86) PCT No.: PCT/CN2021/099437
§ 371 (c)(1),
(2) Date: Sep. 19, 2022

(87) PCT Pub. No.: WO2021/249493
PCT Pub. Date: Dec. 16, 2021

(65) Prior Publication Data
US 2023/0309899 A1     Oct. 5, 2023

(30) Foreign Application Priority Data
Jun. 12, 2020   (CN) .......................... 202010537832.2

(51) Int. Cl.
*A61B 5/355*     (2021.01)
*A61B 5/00*      (2006.01)
*A61B 5/352*     (2021.01)

(52) U.S. Cl.
CPC .............. *A61B 5/355* (2021.01); *A61B 5/352* (2021.01); *A61B 5/726* (2013.01)

(58) Field of Classification Search
None
See application file for complete search history.

(56) References Cited

U.S. PATENT DOCUMENTS 7,729,753 B2 *  6/2010  Kremliovsky ......... A61B 5/349
                                                    600/509
7,751,873 B2     7/2010  de Voir
                         (Continued)

FOREIGN PATENT DOCUMENTS

CN      101766483 A      7/2010
CN      102834050 A     12/2012
                 (Continued)

OTHER PUBLICATIONS

Li Zhan-Ming et al., ECG P/T waves detection algorithm based on stationary wavelet transform, Journal of Lanzhou University of Technology, Jun. 2014, pp. 85-90, vol. 40, No. 3.
(Continued)

*Primary Examiner* — Shirley X Jian
(74) *Attorney, Agent, or Firm* — XSENSUS LLP

(57)                ABSTRACT

A determination method for a beginning of T-wave includes: obtaining an electrocardiogram (ECG) signal; identifying a form of each T-wave in the ECG signal; and recalling a preset algorithm corresponding to the form of the T-wave according to the form of the T-wave to determine a beginning of the T-wave.

17 Claims, 5 Drawing Sheets

(56) References Cited

U.S. PATENT DOCUMENTS

| | | | | |
|---|---|---|---|---|
| 7,881,792 | B1 * | 2/2011 | Farazi ................ | A61N 1/36114 |
| | | | | 607/9 |
| 8,433,395 | B1 * | 4/2013 | Brockway ............ | A61B 5/7203 |
| | | | | 600/509 |
| 2008/0002775 | A1 * | 1/2008 | Ricci ........................ | G06F 18/00 |
| | | | | 375/240.19 |
| 2012/0179055 | A1 * | 7/2012 | Tamil ................... | A61B 5/7465 |
| | | | | 600/509 |
| 2013/0041276 | A1 | 2/2013 | Liao et al. | |
| 2016/0256063 | A1 | 9/2016 | Friedman et al. | |
| 2023/0309899 | A1 * | 10/2023 | Chen ...................... | A61B 5/355 |
| | | | | 600/516 |

FOREIGN PATENT DOCUMENTS

| | | | |
|---|---|---|---|
| CN | 104783786 A | 7/2015 | |
| CN | 109620214 A | 4/2019 | |
| CN | 110013247 A | 7/2019 | |
| CN | 110477906 A | 11/2019 | |
| CN | 111643070 A | 9/2020 | |
| EP | 3 795 074 A1 | 3/2021 | |

OTHER PUBLICATIONS

First Office Action for Chinese Patent Application No. 202010537832.2 issued by the Chinese Patent Office on Jul. 25, 2022.

Jia Hui-Lin et al., Study of Polymorphous T-wave Interval Detection, Progress in Modern Biomedicine, Feb. 2012, pp. 1160-1163, vol. 12, No. 6.

Jinzhong Song et al., A Robust and Efficient Algorithm for ST-T Complex Detection in Electrocardiograms, Journal of Mechanics in Medicine and Biology, Nov. 2011, pp. 1103-1111, vol. 11, No. 5.

Jia Huilin, A study of the technology in the detection of transient T-wave alternans, Master's Thesis of Shandong Normal University, Apr. 8, 2012.

Juan Pablo Martinez et al., A Wavelet-Based ECG Delineator: Evaluation on Standard Databases, IEEE Transactions on Biomedical Engineering, Apr. 2004, pp. 570-581, vol. 51, No. 4.

Yogendra Narain Singh et al., An Efficient and Robust Technique of T Wave Delineation in Electrocardiogram, in Proceedings of the International Conference on Bio-inspired Systems and Signal Processing, 2009, pp. 146-154.

Jiang Yi-Fa et al., An Improved Template-Matching Algorithm and its Application in ECG Waveform Recognition, Chinese Journal of Biomedical Engineering, Oct. 2012, pp. 775-780, vol. 31, No. 5.

Indu Saini et al., Delineation of ECG wave components using K-Nearest Neighbor (KNN) algorithm, 10th International Conference on Information Technology: New Generations, 2013, pp. 712-717.

Cuiwei Li et al., Detection of ECG Characteristic Points Using Wavelet Transforms, IEEE Transactions on Biomedical Engineering, Jan. 1995, pp. 21-28, vol. 42, No. 1.

Research on Feature Extraction and ST Segment Shape Recognition Method for ECG Signal, Chapter IV feature Extract Study of ECG Signals, Master's Thesis, Apr. 2015.

* cited by examiner

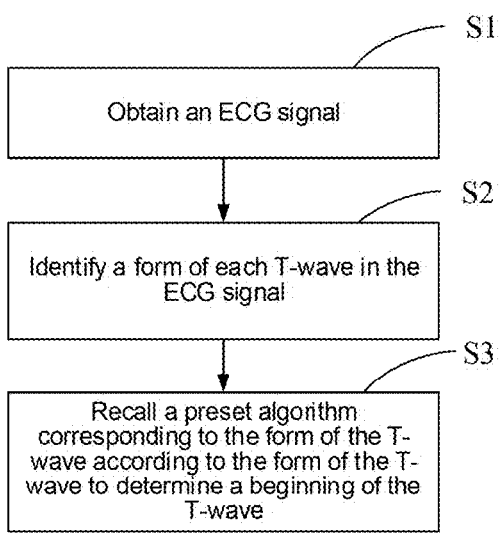

S1

Obtain an ECG signal

S2

Identify a form of each T-wave in the ECG signal

S3

Recall a preset algorithm corresponding to the form of the T-wave according to the form of the T-wave to determine a beginning of the T-wave

FIG. 1

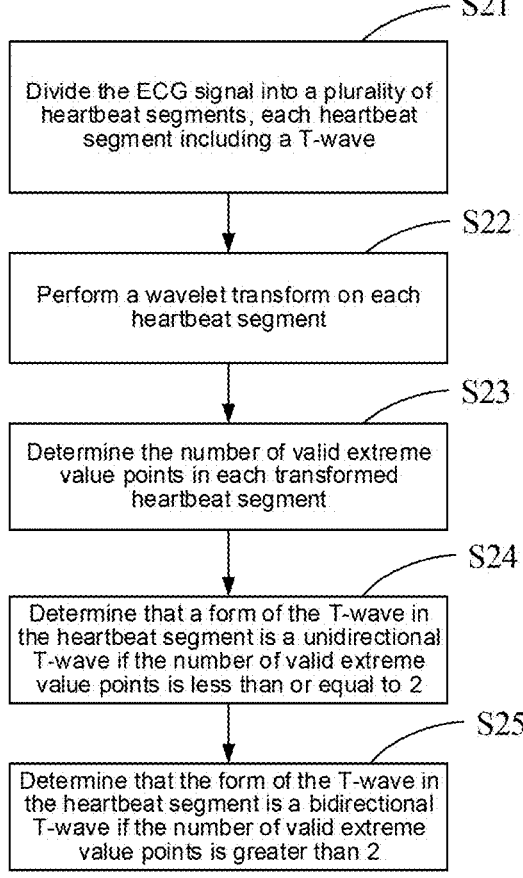

S21

Divide the ECG signal into a plurality of heartbeat segments, each heartbeat segment including a T-wave

S22

Perform a wavelet transform on each heartbeat segment

S23

Determine the number of valid extreme value points in each transformed heartbeat segment

S24

Determine that a form of the T-wave in the heartbeat segment is a unidirectional T-wave if the number of valid extreme value points is less than or equal to 2

S25

Determine that the form of the T-wave in the heartbeat segment is a bidirectional T-wave if the number of valid extreme value points is greater than 2

FIG. 2

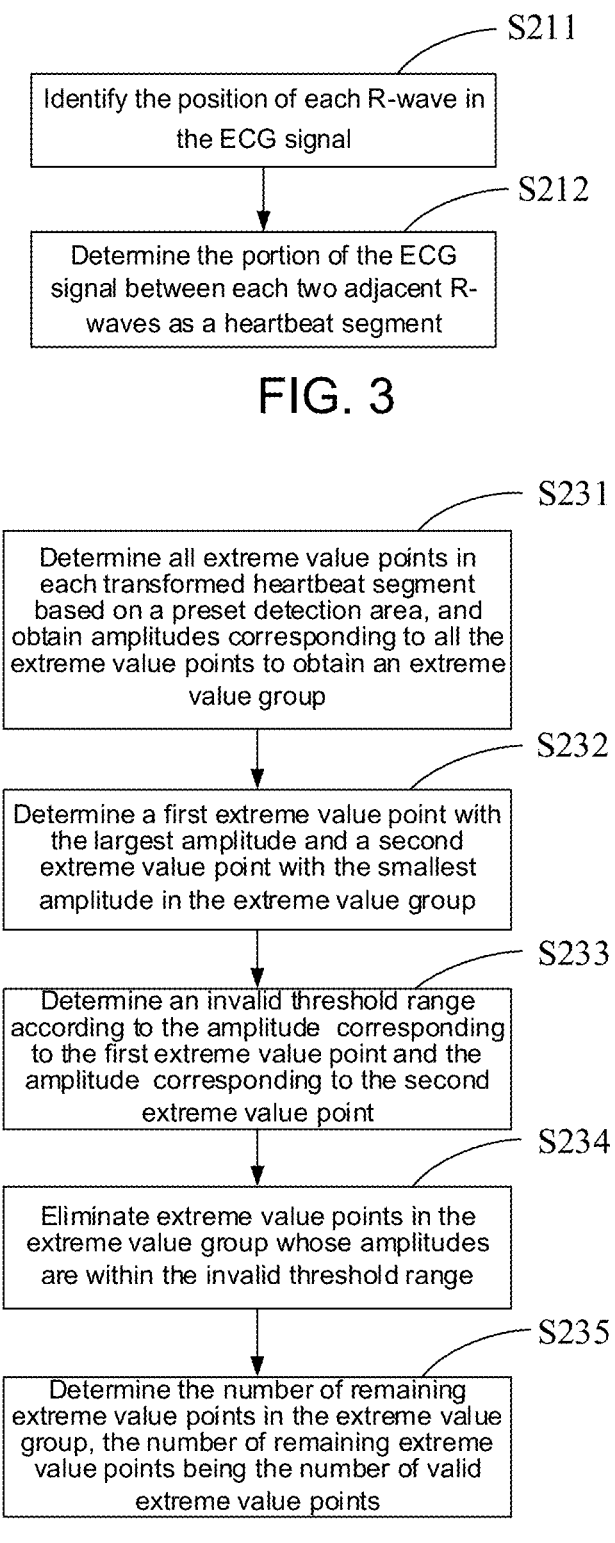

S211

Identify the position of each R-wave in the ECG signal

S212

Determine the portion of the ECG signal between each two adjacent R-waves as a heartbeat segment

Determine all extreme value points in each transformed heartbeat segment based on a preset detection area, and obtain amplitudes corresponding to all the extreme value points to obtain an extreme value group

S232

Determine a first extreme value point with the largest amplitude and a second extreme value point with the smallest amplitude in the extreme value group

S233

Determine an invalid threshold range according to the amplitude corresponding to the first extreme value point and the amplitude corresponding to the second extreme value point

S234

Eliminate extreme value points in the extreme value group whose amplitudes are within the invalid threshold range

S235

Determine the number of remaining extreme value points in the extreme value group, the number of remaining extreme value points being the number of valid extreme value points

FIG. 4

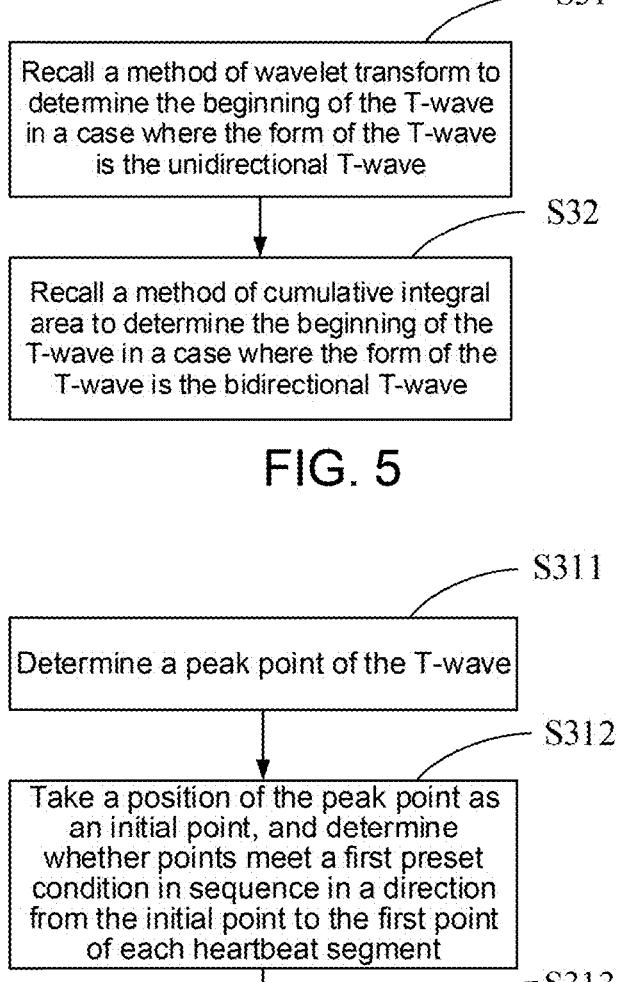

— S31

Recall a method of wavelet transform to determine the beginning of the T-wave in a case where the form of the T-wave is the unidirectional T-wave

— S32

Recall a method of cumulative integral area to determine the beginning of the T-wave in a case where the form of the T-wave is the bidirectional T-wave

Determine a peak point of the T-wave

— S312

Take a position of the peak point as an initial point, and determine whether points meet a first preset condition in sequence in a direction from the initial point to the first point of each heartbeat segment

— S313

Determine a point that first meets the first present condition as the beginning of the T-wave

Determine a first time point and a second time point, the beginning of the T-wave being located between the first time point and the second time point

S322

Determine a window area of each time point between the first time point and the second time point

S323

Determine a time point with a largest window area as the beginning of the T-wave

DETERMINATION METHOD AND DETERMINATION APPARATUS FOR BEGINNING OF T-WAVE, STORAGE MEDIUM AND COMPUTER PROGRAM PRODUCT

CROSS-REFERENCE TO RELATED APPLICATIONS

This application is a national phase entry under 35 USC 371 of International Patent Application No. PCT/CN2021/099437, filed on Jun. 10, 2021, which claims priority to Chinese Patent Application No. 202010537832.2, filed on Jun. 12, 2020, which are incorporated herein by reference in their entirety.

TECHNICAL FIELD

The present disclosure relates to the field of medical data processing, and in particular, to a determination method and a determination apparatus for a beginning of T-wave, a storage medium and a computer program product.

BACKGROUND

T-wave is another important wave band in an electrocardiogram (ECG) signal in addition to QRS wave complex, which is generated by potential changes of ventricular repolarization. In clinical practices, T-wave plays an important role in auxiliary diagnosis.

When T-wave appears inverted, bidirectional or other abnormal form, it has good diagnostic effect on myocardial ischemia, coronary heart disease, etc. Therefore, T-wave is a key indicator in ECG for the diagnosis of myocardial ischemia, coronary heart disease, etc., and an accurate diagnosis of which is directly related to the accurate determination of T-wave.

SUMMARY

In one aspect, a determination method for a beginning of T-wave is provided. The determination method for the beginning of T-wave includes: obtaining an ECG signal; identifying a form of each T-wave in the ECG signal; and recalling a preset algorithm corresponding to the form of the T-wave according to the form of the T-wave to determine a beginning of the T-wave.

In some embodiments, identifying the form of each T-wave in the ECG signal, includes: dividing the ECG signal into a plurality of heartbeat segments, each heartbeat segment including a T-wave; performing a wavelet transform on each heartbeat segment; determining a number of valid extreme value points in each transformed heartbeat segment; determining that a form of the T-wave in the heartbeat segment is a unidirectional T-wave if the number of valid extreme value points is less than or equal to 2: and determining that the form of the T-wave in the heartbeat segment is a bidirectional T-wave if the number of valid extreme value points is greater than 2.

In some embodiments, dividing the ECG signal into the plurality of heartbeat segments, each heartbeat segment including the T-wave, includes: identifying a position of each R-wave in the ECG signal; and determining a portion of the ECG signal between each two adjacent R-waves as a heartbeat segment.

In some embodiments, determining the number of valid extreme value points in each transformed heartbeat segment, includes: determining all extreme value points in each transformed heartbeat segment based on a preset detection area, and obtaining amplitudes corresponding to all the extreme value points to obtain an extreme value group; determining a first extreme value point with a largest amplitude and a second extreme value point with a smallest amplitude in the extreme value group; determining an invalid threshold range according to an amplitude corresponding to the first extreme value point and an amplitude corresponding to the second extreme value point; eliminating extreme value points in the extreme value group whose amplitudes are within the invalid threshold value range; and determining a number of remaining extreme value points in the extreme value group, the number of remaining extreme value points being the number of valid extreme value points.

In some embodiments, recalling the preset algorithm corresponding to the form of the T-wave according to the form of the T-wave to determine the beginning of the T-wave, includes: recalling a method of wavelet transform to determine the beginning of the T-wave a case where the form of the T-wave is the unidirectional T-wave; and recalling a method of cumulative integral area to determine the beginning of the T-wave a case where the form of the T-wave is the bidirectional T-wave.

In some embodiments, recalling the method of wavelet transform to determine the beginning of the T-wave in the case where the form of the T-wave is the unidirectional T-wave, includes: determining a peak point of the T-wave; taking a position of the peak point as an initial point, and determining whether points meet a first preset condition in sequence in a direction from the initial point to a first point of each heartbeat segment; and determining a point that first meets the first present condition as the beginning of the T-wave. The first preset condition is that an amplitude corresponding to the point is less than a preset multiple of an amplitude corresponding to a maximum extremum point closest to the point, and an absolute value of a slope of the point is less than a preset slope.

In some embodiments, the preset multiple is in a range of 0.25 to 0.35, and the preset slope is in a range of 0.25 to 0.35.

In some embodiments, recalling the method of cumulative integral area to determine the beginning of the T-wave in the case where the form of the T-wave is the bidirectional T-wave, includes: determining a first time point and a second time point, the beginning of the T-wave being located between the first time point and the second time point; determining a window area of each time point between the first time point and the second time point; and determining a time point with a largest window area as the beginning of the T-wave.

In another aspect, a determination apparatus for a beginning of T-wave is provided. The determination apparatus for the beginning of T-wave includes a receiving circuit, an identification circuit and a determination circuit. The receiving circuit is configured to obtain an ECG signal. The identification circuit is coupled to the receiving circuit, and the identification circuit is configured to identify a form of each T-wave in the ECG signal. The determination circuit is coupled to the identification circuit, and the determination circuit is configured to, according to the form of the T-wave, recall a preset algorithm corresponding to the form of the T-wave to determine the beginning of the T-wave.

In some embodiments, the identification circuit is configured to: divide the ECG signal into a plurality of heartbeat segments, each heartbeat segment including a T-wave; perform a wavelet transform on each heartbeat segment; determine a number of valid extreme value points in each transformed heartbeat segment; determine that a form of the T-wave in the heartbeat segment is a unidirectional T-wave if the number of valid extreme value points is less than or equal to 2; and determine that the form of the T-wave in the heartbeat segment is a bidirectional T-wave if the number of valid extreme value points is greater than 2.

In some embodiments, in a case where the identification circuit is configured to divide the ECG signal into the plurality of heartbeat segments, the identification circuit is configured to identify a position of each R-wave in the ECG signal, and determine a portion of the ECG signal between each two adjacent R-waves as a heartbeat segment.

In some embodiments, in a case where the identification circuit is configured to determine the number of valid extreme value points in each transformed heartbeat segment, the identification circuit is configured to: determine all extreme value points in each transformed heartbeat segment based on a preset detection area, and obtain amplitudes corresponding to all the extreme value points to obtain an extreme value group; determine a first extreme value point with a largest amplitude and a second extreme value point with a smallest amplitude in the extreme group; determine an invalid threshold range according to an amplitude corresponding to the first extreme value point and an amplitude corresponding to the second extreme value point; eliminate extreme value points in the extreme value group whose amplitudes are within the invalid threshold value range; and determine a number of remaining extreme value points in the extreme value group, the number of remaining extreme value points being the number of valid extreme value points.

In some embodiments, the determination circuit is configured to recall a method of wavelet transform to determine the beginning of the T-wave in a case where the form of the T-wave is the unidirectional T-wave, and recall a method of cumulative integral area to determine the beginning of the T-wave in a case where the form of the T-wave is the bidirectional T-wave.

In some embodiments, in the case where the form of the T-wave is the unidirectional T-wave, the determination circuit is configured to: determine a peak point of the T-wave; take a position of the peak point as an initial point, and determine whether points meet a first preset condition in sequence in a direction from the initial point to a first point of each heartbeat segment; and determine a point that first meets the first present condition as the beginning of the T-wave. The first preset condition is that an amplitude corresponding to the point is less than a preset multiple of an amplitude corresponding to a maximum extremum point closest to the point, and an absolute value of a slope of the point is less than a preset slope.

In some embodiments, in the case where the form of the T-wave is the bidirectional T-wave, the determination circuit is configured to: determine a first time point and a second time point, the beginning of the T-wave being located between the first time point and the second time point; determine a window area of each time point between the first time point and the second time point; and determining a time point with a largest window area as the beginning of the T-wave.

In yet another aspect, a non-transitory computer-readable storage medium is provided. The non-transitory computer-readable storage medium has stored thereon computer program instructions that, when run on a processor, cause the processor to perform one or more steps of the determination method for the beginning of T-wave according to any one of the above embodiments.

In yet another aspect, a computer program product is provided. The computer program product includes computer program instructions that, when executed on a computer, cause the computer to perform one or more steps of the determination method for the beginning of T-wave according to any one of the above embodiments.

BRIEF DESCRIPTION OF THE DRAWINGS

In order to describe technical solutions in the present disclosure more clearly, accompanying drawings to be used in some embodiments of the present disclosure will be introduced briefly below. Obviously, the accompanying drawings to be described below are merely accompanying drawings of some embodiments of the present disclosure, and a person of ordinary skill in the art can obtain other drawings according to these drawings. In addition, the accompanying drawings in the following description may be regarded as schematic diagrams, and are not limitations on actual sizes of products, actual processes of methods and actual timings of signals involved in the embodiments of the present disclosure.

FIG. 1 is a flow diagram of a determination method for a beginning of T-wave, in accordance with some embodiments;

FIG. 2 is another flow diagram of a determination method for a beginning of T-wave, in accordance with some embodiments;

FIG. 3 is yet another flow diagram of a determination method for a beginning of T-wave, in accordance with some embodiments;

FIG. 4 is yet another flow diagram of a determination method for a beginning of T-wave, in accordance with some embodiments;

FIG. 5 is yet another flow diagram of a determination method for a beginning of T-wave, in accordance with some embodiments;

FIG. 6 is yet another flow diagram of a determination method for a beginning of T-wave, in accordance with some embodiments;

DETAILED DESCRIPTION

Figure 7:
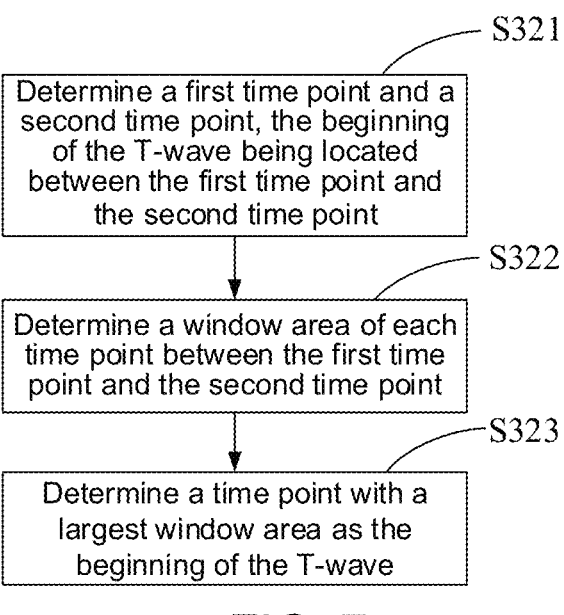
FIG. 7 is yet another flow diagram of a determination method for a beginning of T-wave, in accordance with some embodiments.

Technical solutions in some embodiments of the present disclosure will be described clearly and completely with reference to the accompanying drawings below. Obviously, the described embodiments are merely some but not all embodiments of the present disclosure. All other embodiments obtained by a person of ordinary skill in the art based on the embodiments of the present disclosure shall be included in the protection scope of the present disclosure.

Unless the context requires otherwise, throughout the description and the claims, the term "comprise" and other forms thereof such as the third-person singular form "comprises" and the present participle form "comprising" are construed as open and inclusive meaning, i.e., "including, but not limited to". In the description of the specification, the terms such as "one embodiment", "some embodiments", "exemplary embodiments", "example", "specific example" or "some examples" are intended to indicate that specific features, structures, materials or characteristics related to the embodiment(s) or example(s) are included in at least one embodiment or example of the present disclosure. Schematic representations of the above terms do not necessarily refer to the same embodiment(s) or example(s). In addition, the specific features, structures, materials or characteristics may be included in any one or more embodiments or examples in any suitable manner.

Hereinafter, the terms such as "first" and "second" are used for descriptive purposes only, and are not to be construed as indicating or implying the relative importance or implicitly indicating the number of indicated technical features. Thus, a feature defined with "first" or "second" may explicitly or implicitly include one or more of the features. In the description of the embodiments of the present disclosure, "a plurality of/the plurality of" means two or more unless otherwise specified.

In the description of some embodiments, terms such as "coupled" and "connected" and their extensions may be used. For example, the term "connected" may be used in the description of some embodiments to indicate that two or more components are in direct physical or electrical contact with each other. As another example, the term "coupled" may be used in the description of some embodiments to indicate that two or more components are in direct physical or electrical contact. The term "coupled" or "communicatively coupled", however, may also mean that two or more components are not in direct contact with each other, but still cooperate or interact with each other. The embodiments disclosed herein are not necessarily limited to the content herein.

The phrase "A and/or B" includes the following three combinations: only A, only B, and a combination of A and B.

The use of "applicable to" or "configured to" herein means an open and inclusive expression, which does not exclude devices that are applicable to or configured to perform additional tasks or steps.

Additionally, the use of the phase "based on" is meant to be open and inclusive, since a process, step, calculation or other action that is "based on" one or more of the stated conditions or values may, in practice, be based on additional conditions or value beyond those stated.

The ECG is an objective indicator of the occurrence, propagation and recovery of cardiac excitation. A waveform of the ECG mainly includes QRS wave complex, T-wave and U-wave, each of which represents the changes in the activity of the heart at different times. For example, the QRS wave complex reflects the changes in the depolarization potential and time of the left and right ventricles, the T-wave reflects the process of ventricular repolarization, and the U-wave may be formed by the negative posterior potential generated by parts of the heart during diastole. Therefore, it can be determined whether a person has or may have a heart-related disease by collecting and analyzing the person's ECG signal. The T-wave is a very important wave band in the ECG signal, which has good diagnostic effect on myocardial ischemia, coronary heart disease, etc. Therefore, it is very important to accurately determine a beginning of the T-wave for the analysis of the ECG.

In the related art, there are mainly two types of detection algorithms for the T-wave, which are a detection algorithm based on a threshold and a detection algorithm that does not only rely on a threshold. In the detection algorithm based on the threshold, waveform boundary characteristics are determined by the preset threshold. However, the T-wave may appear inverted, bidirectional or other abnormal form, and in this case, detection accuracy of the detection algorithm based on the preset threshold is low. The detection algorithm that does not only rely on the threshold mainly includes a method of wavelet transform, a method of cumulative integral area, a template matching method, and a statistical pattern recognition, most of which first classify ECG signals and then extract features.

However, it takes a long time to detect the T-wave and determine the beginning of T-wave in the template matching method and statistical pattern recognition, which is very inefficient. The method of wavelet transform and the method of cumulative integral area cannot accurately determine the beginnings for all types of T-waves, which is less adaptable.

Some embodiments of the present disclosure provide a determination method for the beginning of T-wave, so as to accurately determine the beginnings of T-waves of different forms in the ECG signal. As shown in FIG. 1, the determination method for the beginning of T-wave includes S1 to S3.

In S1, the ECG signal is obtained.

Here, the ECG signal may be composed of amplitudes corresponding to a plurality of time points at preset time intervals. The ECG signal may be transmitted by a heart rate detection device, or may be transmitted by an internal memory, which is not limited in the present disclosure.

It will be noted that, the memory may be a read-only memory (ROM) or any other type of static storage device that may store static information and instructions, a random access memory (RAM), or any other type of dynamic storage device that may store information and instructions, or may also be an electrically erasable programmable read-only memory (EEPROM), a magnetic disc storage medium or any other compact disc storage device, or any other medium that may be used to carry or store a desired program code in a form of instructions or data structures and can be accessed by a computer, which is not limited in the present disclosure.

In S2, a form of each T-wave in the ECG signal is identified.

Figure 9A:
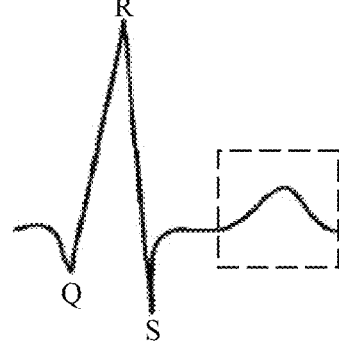
FIG. 9A is a waveform diagram of a T-wave, in accordance with some embodiments.
Figure 9B:
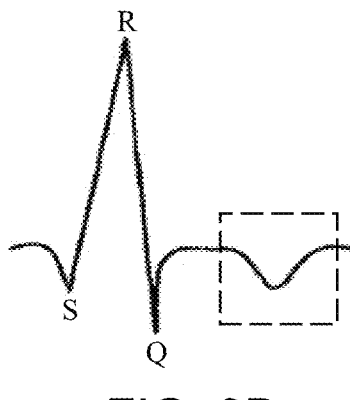
FIG. 9B is a waveform diagram of another T-wave, in accordance with some embodiments.
Figure 10:
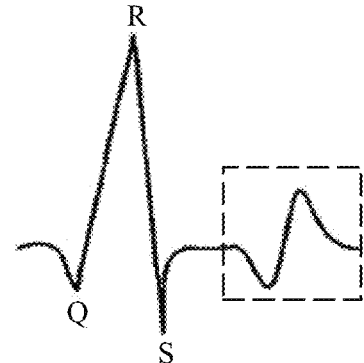
FIG. 10 is a waveform diagram of yet another T-wave, in accordance with some embodiments.

As shown in FIGS. 9A, 98 and 10, T-waves include unidirectional T-waves and a bidirectional T-wave. The unidirectional T-waves include a low-level T-wave (i.e., a normal T-wave) and an inverted T-wave. The part in the dashed box of FIG. 9A is the low-level T-wave, the part in the dashed box of FIG. 98 is the inverted T-wave, and the part in the dashed box of FIG. 10 is the bidirectional T-wave.

In S3, a preset algorithm corresponding to the form of the T-wave is recalled, so as to determine the beginning point of the T-wave.

There are various algorithms for determining the beginning of T-wave of each form, the determination of the beginning of T-wave of each form corresponds an optimal algorithm, and the beginning of T-wave of a corresponding form may be accurately and quickly determined by using the optimal algorithm.

Based on this, after determining the form of each T-wave, according to the form of the T-wave, the preset algorithm corresponding to the form of the T-wave is recalled to determine the beginning of the T-wave; and the preset algorithm is an optimal algorithm for determining the beginning of the T-wave. For example, the optimal algorithm for determining the beginning of the unidirectional T-wave is the method of wavelet change, and the optimal algorithm for determining the beginning of the bidirectional T-wave is the method of cumulative integral area.

In some embodiments of the present disclosure, first, the ECG signal is analyzed to accurately identify the form of each T-wave in the ECG signal; then, according forms of different T-waves, respective optimal algorithms are automatically recalled to determine the beginnings of the T-waves.

For example, in a case where the form of the T-wave is the unidirectional T-wave, the method of wavelet transform is recalled to determine the beginning of the unidirectional T-wave, so as to quickly and accurately determine the beginning of the unidirectional T-wave; in a case where the form of the T-wave is the bidirectional T-wave, the method of cumulative integral area is recalled to determine the beginning of the bidirectional T-wave, so as to quickly and accurately determine the beginning of the bidirectional T-wave.

It can be seen from the above that, in the determination method for the beginning point of T-wave provided in some embodiments of the present disclosure, it may be ensured that the beginning of T-wave of each form is determined by a corresponding preset algorithm (i.e., an optimal algorithm), which improves the adaptability and accuracy of the determination method for the beginning of T-wave.

In some embodiments, as shown in FIG. 2, S2 includes S21 to S24.

In S21, the ECG signal is divided into a plurality of heartbeat segments, and each heartbeat segment includes a T-wave.

Figure 8:
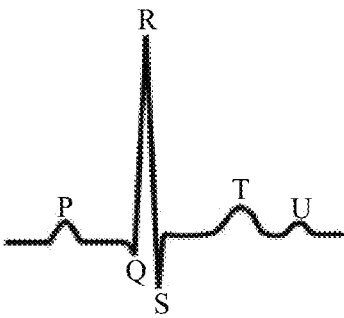
FIG. 8 is a waveform diagram of an ECG signal, in accordance with some embodiments.

Referring to FIG. 8, since the P-wave, QRS wave complex, T-wave and U-wave are usually displayed periodically in the ECG signal, and the T-wave is displayed after the QRS wave complex, there must be one T-wave between two consecutive QRS wave complexes. Therefore, each QRS wave complex in the ECG signal may be identified, and the ECG signal may be divided according to positions where the two consecutive QRS wave complexes are located. A heartbeat segment is located between the two consecutive QRS wave complexes, and each heartbeat segment includes one T-wave.

As shown in FIG. 8, the QRS wave complex reflects the changes in the depolarization potential and time of the left and right ventricles. The first downward wave is a Q-wave, the upward wave is an R-wave, and the next downward wave is an S-wave; and thus, the R-wave in the QRS wave complex is more obvious, Based on this, the ECG signal may be divided by using a position of the R-wave in the QRS wave complex as a reference, and a portion of the ECG signal between each two adjacent R-waves may be determined as a heartbeat segment. In FIG. 8, the T-wave is shown as the low-level T-wave for illustration.

For example, as shown in FIG. 3, S21 includes S211 to S212.

In S211, the position of each R-wave in the ECG signal is identified.

In S212, the portion of the ECG signal between each two adjacent R-waves is determined as a heartbeat segment.

The number of R-waves in the ECG signal is L, $R_l$ represents a position point of a l-th R-wave, and in each heartbeat segment, $x_l(n)=ECG(N)$, l=1, 2, 3, . . . ,L−1, n=1,2,3, . . . , $R_{l+1}-R_l$, N=$R_l$+1, $R_l$+2, . . . , $R_{l+1}$, Where $x_l(n)$ is an amplitude of a n-th point in a I-th heartbeat segment, and ECG(N) is an amplitude of a N-th point in the ECG signal corresponding to the amplitude of the n-th point in I-th heartbeat segment.

In S22, a wavelet transform is performed on each heartbeat segment.

In some embodiments, a binary wavelet is used as a base wavelet to perform the wavelet transform on each heartbeat segment. The binary wavelet is used as the base wavelet to perform the wavelet transform, which is the result of the semi-discretization of the continuous wavelet transform. The scale factor is discretized, and the translation factor takes continuous values; and thus, the result is more accurate. The formulas are as follows:

$$S_{2^j}x_l(n)=\Sigma_{k\in Z}h_k S_{2^{j-1}}x_l(n-2^{j-1}k);$$

$$W_{2^j}x_l(n)=\Sigma_{k\in Z}g_k S_{2^{j-1}}x_l(n-2^{j-1}k);$$

Where $S_{2^j}$ is a smoothing operator; j is a preset scale; $S_{2^j}x_l(n)$ is a low-frequency coefficient of the heartbeat segment, which is used to reflect portion(s) of the heartbeat segment whose change is slow and fluctuation is small, and reflects the overall change of the waveform data; $W_{2^j}x_l(n)$ is a high-frequency coefficient of the heartbeat segment, which is used to reflect portion(s) of the heartbeat segment whose change is drastic and fluctuation (e.g., fluctuation of the R-wave) is large, and reflects the detailed information of the waveform data; $h_k$ and $g_k$ respectively represents a coefficient of a low-pass filter and a coefficient of a high-pass filter, and their specific values are related to the preset scale j; k is an ergodic value within the set of integers; and Z represents the set of integers.

It will be noted that, the preset scale j is selected according to a frequency of the T-wave, and their corresponding relationship is shown in Table I below.

TABLE 1

| Preset scale | Frequency range (Hz) |
|---|---|
| j = 1 | 62.5~125 |
| j = 2 | 18~58.5 |
| j = 3 | 8~27 |
| j = 4 | 4~13.5 |
| j = 5 | 2~6.5 |

It will be noted that, the attenuation of 3 dB is considered when the frequency range is divided, so that the frequency ranges corresponding to different preset scales j are overlapped, Generally, a value of the preset scale j corresponding to the frequency of the T-wave is a serial number of a frequency range in which the frequency of the T-wave is concentrated. For example, the frequency of the T-wave is 7 Hz, and a corresponding preset scale is j=4.

In S23, the number of valid extreme value points in each transformed heartbeat segment is determined.

In a case where the number of valid extreme value points is less than or equal to 2, S24 is executed; and in a case where the number of valid extreme value points is greater than 2, S25 is executed.

In S24, it is determined that the form of the T-wave in the heartbeat segment is the unidirectional T-wave.

In S25, it is determined that the form of the T-wave in the heartbeat segment is the bidirectional T-wave.

It will be noted that, if the number of valid extreme value points is greater than 3, three valid extreme value points having the largest amplitude absolute value and including positive and negative valid extreme value points may be selected from all valid extreme value points, so as to determine that the form of the T-wave in the heartbeat segment is the bidirectional T-wave.

In some embodiments, as shown in FIG. 4, S23 includes S231 to S235.

In S231, all extreme value points in each transformed heartbeat segment based on a preset detection area are determined, and amplitudes corresponding to all the extreme value points are obtained to obtain an extreme value group.

In the case of the preset scale j=4, 0<n<0.3 ($R_{l+1}$–$R_l$) is taken as the preset detection area, so as to determine all the extreme value points in the preset detection area, and obtain the amplitudes $P_l$ corresponding to all the extreme value points. The amplitudes $P_l$ corresponding to all the extreme value points constitute the extreme value group. $P_l$ is an amplitude corresponding to an i-th extreme value point in the extreme value group, i=1,2, 3, . . . m, m is the number of extreme value points in the preset detection area.

In S232, a first extreme value point with the largest amplitude and a second extreme value point with the smallest amplitude in the extreme value group are determined.

For example, the amplitudes $P_l$ corresponding to all the extreme value points i in the extreme value group are compared, so as to screen the extreme value point with the largest amplitude in the extreme value group to be determined as the first extreme value point, the amplitude corresponding to the first extreme value point being $P_{max}$; and screen the extreme value point with the smallest amplitude in the extreme value group to be determined as the second extreme value point, the amplitude corresponding to the second extreme value point being $P_{min}$.

In S233, an invalid threshold range is determined according to the amplitude $P_{max}$ corresponding to the first extreme value point and the amplitude $P_{min}$ corresponding to the second extreme value point.

For example, the invalid threshold range is determined as a range of $P_{min}/6$ to $P_{min}/6$ according to the amplitude max corresponding to the first extreme value point and the amplitude $P_{max}$ corresponding to the second extreme value point.

In S234, extreme value points in the extreme value group whose amplitudes are within the invalid threshold range are eliminated.

For example, the invalid threshold range is the range of $P_{min}/6$ to $P_{max}/6$. Based on the invalid threshold range, all the extreme value points in the extreme value group are screened, and extreme value points are eliminated if the amplitudes $P_l$ corresponding to the extreme value points satisfy a relationship $P_{min}/6<P_l<P_{max}/6$.

In S235, the number of remaining extreme value points in the extreme value group is determined, and the number of remaining extreme value points is the number of valid extreme value points.

In this case, the remaining extreme value points are the valid extreme value points, and amplitudes $P_r$ corresponding to the valid extreme value points constitute a valid extreme value group. $P_r$ is an amplitude corresponding to a r-th valid extreme value point in the valid extreme value group, r=1,2,3, . . . u, u is the number of remaining extreme value points in the extreme value group, i.e., the number of valid extreme value points in the valid extreme value group.

In some embodiments, as shown in FIG. 5, S3 includes S31 to S32.

In S31, the method of wavelet transform is recalled to determine the beginning of the T-wave in a case where the form of the T-wave is the unidirectional T-wave.

In this case, for the unidirectional T-wave, the method of wavelet transform is recalled to determine the beginning of the unidirectional T-wave. In this way, whether the unidirectional T-wave is the low-level T-wave or the inverted T-wave, the method of wavelet transform may be used to quickly and accurately determine the beginning of the T-wave, which takes less time and is more efficient.

For example, as shown in FIG. 6, S31 includes S311 to S313.

In S311, a peak point of the T-wave is determined.

A zero-crossing point between the extreme value points in the preset detection area is the peak point of the T-wave in the heartbeat segment. That is to say, the zero-crossing point between the extreme value points in the preset detection area in each transformed heartbeat segment may be determined as the peak point of the T-wave in the heartbeat segment.

In S312, a position of the peak point is taken as an initial point, and it is determined whether points meet a first preset condition in sequence in a direction from the initial point to the first point of each heartbeat segment.

Here, the first preset condition is that an amplitude corresponding to a point is less than a preset multiple of an amplitude corresponding to a maximum extremum point closest to the point, and an absolute value of a slope of the point is less than a preset slope. The slope of the point is an amplitude of a latter point minus the amplitude of the point.

In some embodiments, the preset multiple is in a range of 0.25 to 0.35, and the preset slope is in a range of 0.25 to 0.35. For example, the preset multiple is 0.25, 0.3, or 0.35, and the preset slope is 0.25, 0.3, or 0.35, which is not limited in the present disclosure.

In S313, a point that first meets the first preset condition is determined as the beginning of the T-wave.

In S32, the method of cumulative integral area is recalled to determine the beginning of the T-wave in a case where the T-wave is the bidirectional T-wave.

In this case, for the bidirectional T-wave, the method of cumulative integral area is recalled to determine the beginning of the T-wave, so as to quickly and accurately determine the beginning of the bidirectional T-wave.

For example, as shown in FIG. 7, S32 includes S321 to S323.

In S321, a first time point $T_a$ and a second time point $T_b$ are determined, and the beginning of the T-wave is between the first time point $T_c$, and the second time point $T_b$.

In a case where the beginning of the T-wave is determined according to the method of cumulative integral area, for each heartbeat segment $x_l(n)$, it is necessary to first determine the range where the beginning of the T-wave is located, so as to reduce the search range of the beginning and the calculation amount. The range where the beginning of the T-wave is located may be determined according to the first time point $T_c$, and the second time point $T_b$, which are respectively obtained according to the following formulas:

$$T_a = \begin{cases} 0.15(R_{l+1} - R_l) + 37, (R_{l+1} - R_l) < 220 \\ R_{l+1} - 2R_l + 70, (R_{l+1} + R_l) \geq 220 \end{cases};$$

$$T_b = \begin{cases} 0.7(R_{l+1} - R_l) - 9, (R_{l+1} - R_l) < 220 \\ 0.2(R_{l+1} - R_l) + 101, (R_{l+1} + R_l) \geq 220 \end{cases}.$$

In S322, a window area D of each time point t between the first time point $T_a$ and the second time point Tr is determined.

Where t=$T_b$,$T_b$–1, . . . $T_a$. The window area $D_t$ corresponding to each time point t is calculated, and the formulas are as follows:

$$\bar{s}_t = \frac{1}{2q+1}\sum_{n=t-q}^{t+q} x_l(n);$$

$$D_t = \sum_{n=t-w+1}^{t} |x_l(n) - \bar{s}_t|.$$

Where w is a width of a sliding window, q is a width of a smooth window, $\bar{s}_t$ is a mean value within the smooth window. The mean value within the smooth window $\bar{s}_t$ is used to eliminate the influence of noise, so as to achieve the effect of smoothing the waveform.

In some embodiments, the width of the sliding window w is in a range of 25 to 35. For example, the width of the sliding window w is 25, 30, or 35, which is not limited in the present disclosure.

In some embodiments, the width of the smooth window q is in a range of 4 to 6. For example, the width of the smooth window q is 4, 5, or 6, which is not limited in the present disclosure.

In S323, a time point $t_{max}$ with the largest window area $D_t$ is determined as the beginning of the T-wave.

Window areas $D_t$ corresponding to time points t are compared, so as to screen the time point $t_{max}$ with the largest window area; and the time point $t_{max}$ is the beginning of the T-wave.

Figure 11:
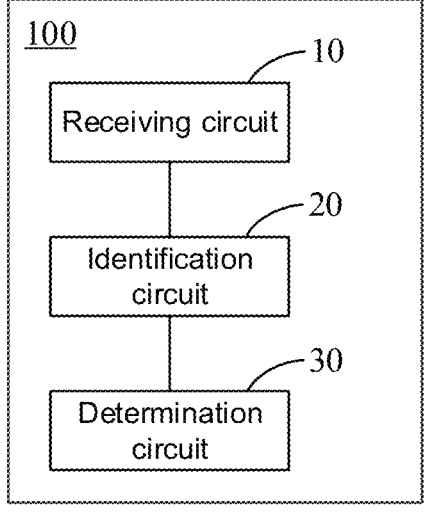
FIG. 11 is a structural diagram of a determination apparatus for a beginning of T-wave, in accordance with some embodiments.

Some embodiments of the present disclosure further provide a determination apparatus 100 for a beginning of T-wave. As shown in FIG. 11, the determination apparatus 100 for the beginning of T-wave includes a receiving circuit 10, an identification circuit 20 and a determination circuit 30. The receiving circuit 10 is configured to obtain an ECG signal. The identification circuit 20 is coupled to the receiving circuit 10, and the identification circuit 20 is configured to identify a form of each T-wave in the ECG signal. The determination circuit 30 is coupled to the identification circuit 20, and the determination circuit 30 is configured to recall a preset algorithm corresponding to the form of the T-wave according to the form of the T-wave, and determine the beginning of the T-wave.

It will be noted that, the ECG signal may be composed of amplitudes corresponding to a plurality of time points at a preset time interval. The ECG signal may be transmitted by a heart rate detection device, or may be transmitted by an internal memory, which is not limited in the present disclosure.

In some embodiments, when the identification circuit 20 identifies the form of each T-wave in the ECG signal, the identification circuit 20 is configured to: divide the ECG signal into a plurality of heartbeat segments, each heartbeat segment including a T-wave; perform wavelet transform on each heartbeat segment; then, determine the number of valid extreme value points in each transformed heartbeat segment; and if the number of valid extreme value points is less than or equal to 2, determine that the form of the T-wave in the heartbeat segment is a unidirectional T-wave: if the number of valid extreme value points is greater than 2, determine that the form of the T-wave in the heartbeat segment is a bidirectional T-wave.

In some embodiments, when the identification circuit 20 divides the ECG signal, the identification circuit 20 is configured to first identify a position of each R-wave in the ECG signal, and then determine a portion of the ECG signal between each two adjacent R-waves as a heartbeat segment.

In some embodiments, when the identification circuit 20 determines the number of valid extreme value points in each transformed heartbeat segment, the identification circuit 20 is configured to: determine all extreme value points in each transformed heartbeat segment based on a preset detection area; obtain amplitudes corresponding to all extreme value points to obtain an extreme value group; determine a first extreme value point with the largest amplitude and a second extreme value point with the smallest amplitude in the extreme value group; determine an invalid threshold range according to the amplitude corresponding to the first extreme value and the amplitude corresponding to the second extreme value; eliminate extreme value points in the extreme value group whose amplitudes are within the invalid threshold range; and determine the number of remaining extreme value points in the extreme value group, the number of remaining extreme value points being the number of valid extreme value points.

It will be noted that, the algorithm and beneficial effects of the identification circuit for identifying the form of the T-wave are described in detail in the above determination method for the beginning of T-wave, and will not be described here again.

In some embodiments, when the determination circuit 30 determines the beginnings of T-waves of different forms by recalling respective preset algorithms based on the identification result of the identification circuit 20, the determination circuit 30 is configured to recall the method of wavelet transform to determine the beginning of the T-wave in a case where the form of the T-wave is the unidirectional T-wave, and recall the method of cumulative integral area to determine the beginning of the T-wave in a case where the form of the T-wave is the bidirectional T-wave. In this case, after obtaining the identification result of the identification circuit 20, the determination circuit 30 may automatically recall the corresponding algorithm to determine the beginning of the T-wave, so as to improve the adaptability and accuracy of determining the beginning of the T-wave.

In some embodiments, when the method of wavelet transform is recalled to determine the beginning of the T-wave, the determination circuit 30 is configured to: determine a peak point of the T-wave; take a position of the peak point as an initial point; determine whether points meet a first preset condition in sequence in a direction from the initial point to the first point of each heartbeat segment; and determine a point that first meets the first preset condition as the beginning of the T-wave. The first preset condition is that an amplitude corresponding to a point is less than a preset multiple of an amplitude corresponding to a maximum extremum point closest to the point, and an absolute value of a slope of the point is less than a preset slope.

Here, the first preset condition is that the amplitude corresponding to the point is less than the preset multiple of the amplitude corresponding to the maximum extremum point closest to the point, and the absolute value of the slope of the point is less than the preset slope. The slope of the point is an amplitude of a latter point minus the amplitude of the point.

In some embodiments, the preset multiple is in a range of 0.25 to 0.35, and the preset slope is in a range of 0.25 to 0.35. For example, the preset multiple is 0.25, 0.3, or 0.35, and the preset slope is 0.25, 0.3, or 0.35, which is not limited in the present disclosure.

In some embodiments, when the determination circuit 30 recalls the method of cumulative integral area to determine the beginning of the T-wave, the determination circuit is configured to: determine a first time point and a second time point, the beginning of the T-wave being located between the first time point and the second time point; determine a window area of each time point between the first time point and the second time point; and determine a time point with the largest window area as the beginning of the T-wave.

It will be noted that, the algorithm and beneficial effects of the determination circuit for determining the beginning of T-wave are described in detail in the above determination method for the beginning of T-wave, and will not be described here again.

In some embodiments of the present disclosure, by analyzing the ECG signal to accurately determine the form of each T-wave in the ECG signal, it is possible to automatically select respective optimal algorithms according to different forms of T-waves, so as to determine the beginning of the T-wave. For example, in a case where the T-wave is the unidirectional T-wave, the method of wavelet transform is used to increase the speed for determining the beginning of the unidirectional T-wave; in a case where the T-wave is the bidirectional T-wave, the method of cumulative integral area is used to ensure the accuracy for determining the beginning of the bidirectional T-wave. It can be seen from the above, for the determination apparatus 100 for the beginning of T-wave provided in some embodiments of the present disclosure, it may ensure that the beginning of each T-wave is determined by a corresponding algorithm, which improves the adaptability and accuracy for determining the beginning of the T-wave.

Some embodiments of the present disclosure provide a computer-readable storage medium (e.g., a non-transitory computer-readable storage medium). The computer-readable storage medium has stored thereon computer program instructions that, when run on a computer, cause the computer to execute the determination method for the beginning of T-wave as described in any one of the above embodiments.

For example, the computer-readable storage medium includes, but is not limited to, a magnetic storage device (e.g., a hard disk, a floppy disk or a magnetic tape), an optical disk (e.g., a compact disk (CD), a digital versatile disk (DVD)), a smart card, a flash memory device (e.g., an erasable programmable read-only memory (EPROM)), a card, a stick or a key driver. Various computer-readable storage media described in the embodiments of the present disclosure may represent one or more devices and/or other machine-readable storage media, which are used for storing information. The term "machine-readable storage media" may include, but are not limited to, wireless channel and various other media capable of storing, containing and/or carrying instructions and/or data.

Some embodiments of the present disclosure further provide a computer program product. The computer program product includes computer program instructions that, when run on a computer, cause the computer to execute the determination method for the beginning of T-wave as described in any one of the above embodiments.

Some embodiments of the present disclosure further provide a computer program. When executed on a computer, the computer program causes the computer to execute the determination method for the beginning of T-wave as described in any one of the above embodiments.

Beneficial effects of the computer-readable storage medium, the computer program product and the computer program are the same as the beneficial effects of the determination method for the beginning of T-wave as described in some of the above embodiments, which will not be described here again.

The foregoing descriptions are merely specific implementations of the present disclosure, but the protection scope of the present disclosure is not limited thereto, Changes or replacements that any person skilled in the art could conceive of within the technical scope of the present disclosure shall be included in the protection scope of the present disclosure. Therefore, the protection scope of the present disclosure shall be subject to the protection scope of the claims.

What is claimed is:

1. A determination method for a beginning of T-wave applied to an electrocardiogram (ECG), comprising:

obtaining an ECG signal;

identifying a form of each T-wave in the ECG signal; and recalling a preset algorithm corresponding to a form of an identified T-wave according to the form of the identified T-wave to determine a beginning of the identified T-wave automatically; wherein the ECG is analyzed according to the beginning of the identified T-wave;

wherein identifying the form of each T-wave in the ECG signal, includes:

dividing the ECG signal into a plurality of heartbeat segments, each heartbeat segment including a T-wave;

performing a wavelet transform on each heartbeat segment;

determining a number of valid extreme value points in each transformed heartbeat segment;

determining that a form of the T-wave in the heartbeat segment is a unidirectional T-wave in a case where the number of valid extreme value points is less than or equal to 2; and determining that the form of the T-wave in the heartbeat segment is a bidirectional T-wave in a case where the number of valid extreme value points is greater than 2.

2. The determination method according to claim 1, wherein dividing the ECG signal into the plurality of heartbeat segments includes:

identifying a position of each R-wave in the ECG signal; and determining a portion of the ECG signal between each two adjacent R-waves as a heartbeat segment.

3. The determination method according to claim 2, wherein determining the number of valid extreme value points in each transformed heartbeat segment, includes:

determining all extreme value points in each transformed heartbeat segment based on a preset detection area; wherein the preset detection area is a portion of each transformed heartbeat segment;

obtaining amplitudes corresponding to all the extreme value points to obtain an extreme value group;

determining a first extreme value point with a largest amplitude and a second extreme value point with a smallest amplitude in the extreme value group;

determining an invalid threshold range according to an amplitude corresponding to the first extreme value point and an amplitude corresponding to the second extreme value point;

eliminating extreme value points in the extreme value group whose amplitudes are within the invalid threshold value range; and determining a number of remaining extreme value points in the extreme value group, the number of remaining extreme value points being the number of valid extreme value points.

4. The determination method according to claim 1, wherein determining the number of valid extreme value points in each transformed heartbeat segment, includes:

determining all extreme value points in each transformed heartbeat segment based on a preset detection area;

wherein the preset detection area is a portion of each transformed heartbeat segment;

obtaining amplitudes corresponding to all the extreme value points to obtain an extreme value group;

determining a first extreme value point with a largest amplitude and a second extreme value point with a smallest amplitude in the extreme value group;

determining an invalid threshold range according to an amplitude corresponding to the first extreme value point and an amplitude corresponding to the second extreme value point;

eliminating extreme value points in the extreme value group whose amplitudes are within the invalid threshold value range; and determining a number of remaining extreme value points in the extreme value group, the number of remaining extreme value points being the number of valid extreme value points.

5. The determination method according to claim 1, wherein recalling the preset algorithm corresponding to the form of the identified T-wave according to the form of the identified T-wave to determine the beginning of the identified T-wave automatically, includes:

recalling a method of wavelet transform to determine the beginning of the identified T-wave in a case where the form of the identified T-wave is the unidirectional T-wave; and recalling a method of cumulative integral area to determine the beginning of the identified T-wave in a case where the form of the identified T-wave is the bidirectional T-wave.

6. The determination method according to claim 5, wherein recalling the method of wavelet transform to determine the beginning of the identified T-wave in the case where the form of the identified T-wave is the unidirectional T-wave, includes:

determining a peak point of the identified T-wave;

taking a position of the peak point as an initial point;

in a direction from the initial point to a first point of each heartbeat segment, determining whether points of each heartbeat segment meet a first preset condition in sequence; and determining a point that first meets the first preset condition as the beginning of the identified T-wave;

wherein the first preset condition is that an amplitude corresponding to one point of the points of each heartbeat segment is less than a preset multiple of an amplitude corresponding to a maximum extremum point closest to the one point, and an absolute value of a slope of the one point is less than a preset slope.

7. The determination method according to claim 6, wherein the preset multiple is in a range of 0.25 to 0.35, and the preset slope is in a range of 0.25 to 0.35.

8. The determination method according to claim 5, wherein recalling the method of cumulative integral area to determine the beginning of the identified T-wave in the case where the form of the identified T-wave is the bidirectional T-wave, includes:

determining a first time point and a second time point, the beginning of the identified T-wave being located between the first time point and the second time point;

determining a window area of each time point between the first time point and the second time point; and determining a time point with a largest window area as the beginning of the identified T-wave.

9. A determination apparatus for a beginning of T-wave applied to an electrocardiogram (ECG), comprising:

a receiving circuit configured to obtain an ECG signal;

an identification circuit coupled to the receiving circuit, the identification circuit being configured to identify a form of each T-wave in the ECG signal; and a determination circuit coupled to the identification circuit, the determination circuit being configured to, according to a form of an identified T-wave, recall a preset algorithm corresponding to the form of the identified T-wave to determine a beginning of the identified T-wave automatically; wherein the ECG is analyzed according to the beginning of the identified T-wave;

the identification circuit is configured to:

divide the ECG signal into a plurality of heartbeat segments, each heartbeat segment including a T-wave;

perform a wavelet transform on each heartbeat segment; determine a number of valid extreme value points in each transformed heartbeat segment;

determine that a form of the T-wave in the heartbeat segment is a unidirectional T-wave in a case where the number of valid extreme value points is less than or equal to 2; and determine that the form of the T-wave in the heartbeat segment is a bidirectional T-wave in a case where the number of valid extreme value points is greater than 2.

10. The determination apparatus according to claim 9, wherein in a case where the identification circuit is configured to divide the ECG signal into the plurality of heartbeat segments, the identification circuit is configured to identify a position of each R-wave in the ECG signal, and determine a portion of the ECG signal between each two adjacent R-waves as a heartbeat segment.

11. The determination apparatus according to claim 10, wherein in a case where the identification circuit is configured to determine the number of valid extreme value points in each transformed heartbeat segment, the identification circuit is configured to:

determine all extreme value points in each transformed heartbeat segment based on a preset detection area, and obtain amplitudes corresponding to all the extreme value points to obtain an extreme value group; wherein the preset detection area is a portion of each transformed heartbeat segment;

determine a first extreme value point with a largest amplitude and a second extreme value point with a smallest amplitude in the extreme group;

determine an invalid threshold range according to an amplitude corresponding to the first extreme value point and an amplitude corresponding to the second extreme value point;

eliminate extreme value points in the extreme value group whose amplitudes are within the invalid threshold value range; and determine a number of remaining extreme value points in the extreme value group, the number of remaining extreme value points being the number of valid extreme value points.

12. The determination apparatus according to claim 9, wherein in a case where the identification circuit is configured to determine the number of valid extreme value points in each transformed heartbeat segment, the identification circuit is configured to: determine all extreme value points in each transformed heartbeat segment based on a preset detection area, and obtain amplitudes corresponding to all the extreme value points to obtain an extreme value group; determine a first extreme value point with a largest amplitude and a second extreme value point with a smallest amplitude in the extreme group; determine an invalid threshold range according to an amplitude corresponding to the first extreme value point and an amplitude corresponding to the second extreme value point; eliminate extreme value points in the extreme value group whose amplitudes are within the invalid threshold value range; and determine a number of remaining extreme value points in the extreme value group, the number of remaining extreme value points being the number of valid extreme value points.

13. The determination apparatus according to claim 9, wherein the determination circuit is configured to recall a method of wavelet transform to determine the beginning of the identified T-wave in a case where the form of the identified T-wave is the unidirectional T-wave, and recall a method of cumulative integral area to determine the beginning of the identified T-wave in a case where the form of the identified T-wave is the bidirectional T-wave.

14. The determination apparatus according to claim 13, wherein in the case where the form of the identified T-wave is the unidirectional T-wave, the determination circuit is configured to: determine a peak point of the identified T-wave; take a position of the peak point as an initial point, and determine whether points meet a first preset condition in sequence in a direction from the initial point to a first point of each heartbeat segment; and determine a point that first meets the first preset condition as the beginning of the identified T-wave; wherein the first preset condition is that an amplitude corresponding to one point of the points of each heartbeat segment is less than a preset multiple of an amplitude corresponding to a maximum extremum point closest to the one point, and an absolute value of a slope of the one point is less than a preset slope.

15. The determination apparatus according to claim 13, wherein in the case where the form of the identified T-wave is the bidirectional T-wave, the determination circuit is configured to: determine a first time point and a second time point, the beginning of the identified T-wave being located between the first time point and the second time point; determine a window area of each time point between the first time point and the second time point; and determining a time point with a largest window area as the beginning of the identified T-wave.

16. A non-transitory computer-readable storage medium, wherein the non-transitory computer-readable storage medium has stored thereon computer program instructions that, when run on a processor, cause the processor to perform one or more steps of the determination method for the beginning of T-wave according to claim 1.

17. A computer program product, comprising non-transitory computer program instructions that, when executed on a computer, cause the computer to perform one or more steps of the determination method for the beginning of T-wave according to claim 1.

* * * * *